United States Patent [19]

Gay et al.

[11] Patent Number: 5,124,380
[45] Date of Patent: Jun. 23, 1992

[54] STABILIZED ORGANIC POLYMER COMPOSITIONS CONTAINING COMPOUND CONTAINING A PIPERIDINYL GROUP AND A CARBONATE GROUP

[75] Inventors: Michel Gay, Villeurbanne; Sylvie Lavault, Lyons, both of France

[73] Assignee: Rhone-Poulenc Chimie, Cedex, France

[21] Appl. No.: 725,079

[22] Filed: Jul. 3, 1991

[30] Foreign Application Priority Data

Jul. 3, 1990 [FR] France ................. 90 08659

[51] Int. Cl.⁵ ........................... C08K 5/3435
[52] U.S. Cl. ...................... 524/99; 546/222
[58] Field of Search ............. 524/99; 546/222

[56] References Cited

U.S. PATENT DOCUMENTS

| | | | |
|---|---|---|---|
| 4,115,476 | 9/1978 | Minagawa et al. | 524/99 |
| 4,116,933 | 9/1978 | Ramey et al. | 524/99 |
| 4,124,564 | 11/1978 | Minagawa et al. | 524/99 |
| 4,812,500 | 3/1989 | Hayden | 524/99 |

FOREIGN PATENT DOCUMENTS

0094048A2  5/1983  European Pat. Off.

*Primary Examiner*—Paul R. Michl
*Assistant Examiner*—Tae H. Yoon
*Attorney, Agent, or Firm*—Finnegan, Henderson, Farabow, Garrett and Dunner

[57] ABSTRACT

Compounds containing a 2,2,6,6-tetramethylpiperidinyl group and a method of making them. The compounds are effective for the protection of organic polymers against degradation due to light and ultraviolet radiation.

5 Claims, No Drawings

STABILIZED ORGANIC POLYMER COMPOSITIONS CONTAINING COMPOUND CONTAINING A PIPERIDINYL GROUP AND A CARBONATE GROUP

The present invention relates to new compounds containing a substituted piperidinyl group, more particularly a 2,2,6,6-tetramethylpiperidinyl group. It further relates to the use of these compounds as additives in organic polymers.

More particularly, the present invention relates to new compounds containing a 2,2,6,6-tetramethylpiperidinyl group. These compounds are relatively simple to synthesize and are effective for the protection of polymers against degradation due to light, for example, ultraviolet radiation.

The compounds of the invention are compounds containing a 2,2,6,6-tetramethylpiperidinyl group, which correspond to the general formula (I):

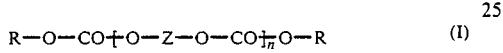

$$R-O-CO+O-Z-O-CO)_{\overline{n}}O-R \quad (I)$$

in which:

R represents:
- a straight-chain or branched alkyl radical having 1 to 18 carbon atoms,
- a cycloalkyl radical having 5 to 12 carbon atoms,
- a phenyl radical,
- a phenyl radical containing 1 or 2 straight chain or branched alkyl substituents having 1 to 12 carbon atoms,
- a phenylalkyl radical in which the straight-chain or branched alkyl portion contains 1 to 12 carbon atoms, or
- a 2,2,6,6-tetramethyl-4-piperidinyl radical of the formula (II)

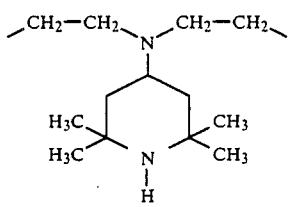

in which $R_1$ represents a hydrogen atom or a methyl radical, and

Z represents:
a radical of the formula (III)

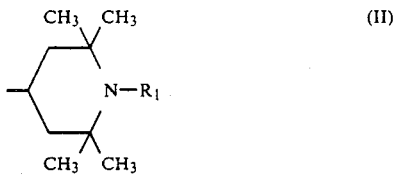

or
a polymethylene group having 2 to 15 carbon atoms, provided that, when Z is a polymethylene group, R is a 2,2,6,6-tetramethyl-4-piperidinyl radical of the formula (II) and n is a number from 1 to 2, and when Z is a radical of the formula (III), n represents a number from 1 to 100.

The compounds of the invention are preferably the compounds the general formula (I) in which:

R represents:
- a methyl, ethyl, propyl, isopropyl, butyl, tert-butyl, hexyl, octyl, decyl, dodecyl, hexadecyl or octadecyl radical,
- a cyclohexyl radical,
- a phenyl radical,
- a phenyl radical containing 1 to 2 straight-chain or branched alkyl substituents having 1 to 9 carbon atoms, such as a methylphenyl radical, a dimethylphenyl radical, an isopropylphenyl radical, a diisopropylphenyl radical, a tert-butylphenyl radical, a di-tert-butylphenyl radical, a nonylphenyl radical or a dinonylphenyl radical,
- a phenylalkyl radical in which the straight-chain or branched alkyl portion contains 1 to 4 carbon atoms, such as a benzyl, a phenylethyl or a 3-phenylpropyl radical, or
- a 2,2,6,6-tetramethyl-4-piperidinyl radical of the formula (II) and Z represents a radical of the formula (III) or a polymethylene group having 2 to 15 carbon atoms, provided that when Z is a polymethylene group, R represents a 2,2,6,6-tetramethyl-4-piperidinyl radical of the formula (II) and n represents a number from 1 to 2, and when Z is a radical of formula (III), n represents a number from 1 to 20.

The compounds of the formula (I) according to the invention may be prepared by a number of methods.

According to a first method when Z is a radical of the formula (III), it is possible first to react a diol of the general formula (IV):

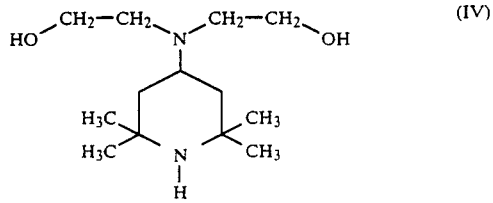

with a stoichiometric excess of dimethyl carbonate in the presence of a basic transesterification catalyst, such as an alkali metal carbonate, an alkali metal alcoholate or an alkali metal hydroxide, and more preferably in the presence of a cryptand such as a crown ether.

The 4-[N,N-bis(ethylene)amino]-2,2,6,6-tetramethylpiperidine bis(dimethyl carbonate) thus obtained, of the formula (V)

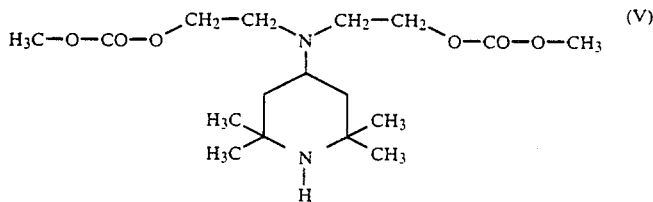

may be converted to a compound of the formula (I) by again reacting the diol of the formula (IV), if a number n of units higher than 1 is desired, with a monoalcohol or a monophenol of the formula (VI):

R'—OH (VI)

in which R' has the meanings indicated above for R in the formula (I).

The ratios of the various reagents of the formulas (IV), (V) and (VI) are selected depending on the number n of units desired:
- (n−1/2) moles of a compound of the formula (IV) and 2 moles of a compound R'—OH of the formula (VI) are used per (n+1/2) moles of a compound of the formula (V).

Any excess dimethyl carbonate can conveniently be removed at the end of the first transesterification reaction, for example by distillation under reduced pressure. The compounds of the formulas (IV) and (VI) may then be added to the compound of the formula (V) containing the catalyst.

In order to prepare the compounds of formula (I) in which Z is a polymethylene radical, a mixed dimethyl polymethylene carbonate of the formula (VII):

$$CH_3-O-CO-[(CH_2)_p-O-CO-]_n-O-CH_3 \quad (VII)$$

in which n has the meanings indicated above for the formula (I) and p represents an integer from 2 to 15, is first prepared by the reaction of a diol of the formula (VIII)

$$HO-(CH_2)_p-OH \quad (VIII)$$

and an excess of dimethyl carbonate, in the presence of a transesterification catalyst as indicated above.

Transesterification between the compound of the formula (VII) and a 2,2,6,6-tetramethylpiperidinol of the formula (IX)

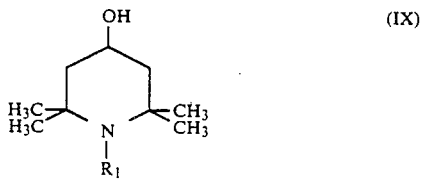

in which $R_1$ is hydrogen or a methyl group, is then carried out.

The compounds of the formula (I) may be monomers or polymers, depending upon the value of the symbol n.

Accordingly, the invention provides molecules of diverse masses. This enables their applications as, for example, anti-UV agents, to be adapted to the various requirements, such as easier migration within the polymer for bulk articles, permanency of the stabilizing effect with time in thin films, etc.

The compounds of formula (I) are preferably used as light stabilizers in organic polymers. More preferably, they may be used as anti-UV agents in polyolefins, polystyrenes, polyalcadienes, polyurethanes, polyamides, polyesters, polycarbonates, polysulfones, polyether sulfones, polyether ketones, acrylic polymers, halogenated polymers, their copolymers and mixtures thereof The compounds of formula (I) are most preferably used in polyolefins and polyalcadienes, such as polypropylene, high density polyethylene, low density polyethylene, straight-chain low density polyethylene, polybutadiene, their copolymers or mixtures thereof.

Another object of the present invention is to provide organic polymer compositions stabilized against the harmful effects of light and ultraviolet radiation by means of an effective amount of at least one compound of the formula (I) containing a 2,2,6,6-tetramethylpiperidinyl group.

These compositions preferably contain from 0.004 to 20 milliequivalents of the 2,2,6,6-tetramethylpiperidinyl group per 100 g of polymer.

More preferably, the polymer compositions stabilized according to the invention contain from 0.020 to 4 milliequivalents of the 2,2,6,6-tetramethylpiperidinyl group per 100 g of polymer.

By way of illustration, the stabilized polymer compositions preferably contain from 0.01% to 5% by weight of a compound of the formula (I) containing a 2,2,6,6-tetramethylpiperidinyl group. The addition of the compounds of the formula (I) may be carried out during or after the preparation of the polymers.

These organic polymer compositions containing the compounds of formula (I) may optionally contain one or more additives or stabilizers which are well known within the art. The additives and stabilizers include, for example:

antioxidants, such as alkylated monophenols, alkylated hydroquinones, hydroxylated diphenyl sulfides, alkylidene-bis-phenols, benzyl compounds, acylaminophenols, 3-(3,5-di-tert-butyl-4-hydroxyphenyl) propionic acid esters, 3-(5-tert-butyl-4-hydroxy-3-methylphenyl) propionic acid esters, 3-(3,5-dicyclohexyl-4-hydroxyphenyl) propionic acid esters and 3-(3,5-di-tert-butyl-4-hydroxyphenyl) propionic acid amides;

ultraviolet radiation absorbers and light stabilizers, such as 2-(2'-hydroxyphenyl)benzotriazoles, 2-hydroxybenzophenones, substituted benzoic acid esters, acrylates, nickel compounds and oxalamides;

metal deactivators;

phosphites and phosphonites;

compounds which destroy peroxides;

nucleating agents;

reinforcing fillers and agents;

plasticizers;

lubricants;

emulsifiers;
pigments;
fluorescent brighteners;
fireproofing agents;
antistatic agents; and
pore-forming agents.

The stabilized polymer compositions may be used in a number of very diverse forms, for example, as molded articles, sheets, fibers, (mass) cellular materials, sections or coating products, sheet-forming agents, (binders) for paints, varnishes, adhesives or cements.

The examples which follow are illustrative of the invention, but are not considered to be limiting.

EXAMPLE 1

Preparation of product (Ia):
4-(N,N-diethyleneamino)-2,2,6,6-tetramethypiperidine bis(dimethyl carbonate)

This is a compound of the formula (I) in which:
R = methyl radical
n = 1
Z = radical of formula (III)

The following were charged into a 500 cm$^3$ round-bottomed flask fitted with a central stirrer, a thermometer pocket, a lateral nitrogen inlet tube and a distillation column:

216 g (2.4 mol) of dimethyl carbonate,
48.8 g (0.2 mol) of 4-[N,N-bis(hydroxyethyl)-amino]-2,2,6,6-tetramethylpiperidine, and
0.008 g of sodium hydroxide in powder form.

The reaction mixture was heated at 92°–95° C. for 5 hours under a stream of nitrogen. During this stage a methanol/dimethyl carbonate binary mixture was distilled (between 63° C. and 70° C.) while a high reflux rate was maintained.

The temperature was then raised to 120° C. for 2 hours, with continuing distillation of the volatile fraction.

In total, 175 g were distilled.

The remainder of the volatile products were then removed at 120° C., while progressively lowering the pressure down to 133 Pa. A further 15 g of volatile products were thus obtained.

70.2 g of a slightly yellow viscous oil were finally obtained.

IR spectrometry and nuclear magnetic resonance (NMR) analyses confirmed the expected structure of the product, the purity of which was higher than 95%.

EXAMPLE 2

Preparation of product (Ib):
pentakis[4-(N,N-diethyleneamino)-2,2,6,6-tetramethylpiperidine] hexakis(dimethyl carbonate)

This is a compound of the general formula (I) in which:
R = methyl radical
n = 5
Z = radical of formula (III)

The following were charged into a 200 cm$^3$ round-bottomed flask fitted with a central stirrer, a thermometer pocket and a distillation column:

43.2 g (0.12 mol) of the product (Ia) prepared in Example 1,
19.5 g (0.08 mol) of 4-[N,N-bis(hydroxyethyl)amino]-2,2,6,6-tetramethylpiperidine,
0.019 of potassium carbonate, and
5 microliters of $C_{18/6}$ crown ether.

The reaction mixture was heated at 105° C. for 4 hours under a pressure of 26,600 Pa.

The pressure was then progressively lowered down to 27 Pa, and the temperature was maintained at 100°–105° C. for 2 hours, removing the methanol at the rate at which it was formed.

58.6 g of a yellow viscous oil were finally obtained.

IR spectrometry and NMR analyses confirmed the expected structure of the product.

EXAMPLE 3

Preparation of product (Ic):
4-(N,N-diethyleneamino)-2,2,6,6-piperidine bis[bis(2,2,6,6-tetramethyl-4-piperidinyl) carbonate]

A compound of the general formula (I) in which:
R = radical of formula (II) where $R_1$ = H
n = 1
Z = radical of formula (III)

The following were charged into a 200 cm$^3$ roundbottomed flask fitted with a central stirrer, a thermometer pocket and a distillation column:

36 g (0.1 mol) of the product (Ia) prepared in Example 1,
31.4 g (0.2 mol) of 4-hydroxy-2,2,6,6-tetramethylpiperidine,
0.0165 g of potassium carbonate, and
5 microliters of $C_{18/6}$ crown ether.

The reaction mixture was heated at 110°–115° C. for 7 hours under a nitrogen atmosphere and then for 2 hours under a pressure of 26,600 Pa.

The pressure was then progressively lowered down to 665 Pa and the temperature was maintained at 115° C. for 30 minutes.

During these operations, the methanol was removed at the rate at which it was formed, and small amounts of 4-hydroxy-2,2,6,6-tetramethylpiperidine were also removed.

The removal of the volatile compounds from the reaction mixture was completed by heating at 120° C. under 266 Pa for 2 hours.

55 g of a yellow highly viscous oil were finally obtained.

NMR analysis shows that this oil was a mixture corresponding to:
starting compound (Ia): 10 mol %
expected product (Ic): 90 mol %

EXAMPLE 4

Preparation of product (Id):
decakis[4-(N,N-diethyleneamino)-2,2,6,6-tetramethylpiperidine] undecakis[bis(2,2,6,6-tetramethyl-4-piperidinyl) carbonate]

A compound of the general formula (I) in which:
R = radical of formula (II) where $R_1$ = H
n = 10
Z = radical of formula (III)

The following were charged into a 200 cm$^3$ roundbottomed flask fitted with a central stirrer, a thermometer and a distillation column:

39.6 g (0.11 mol) of product (Ia) prepared in Example 1,
22.0 g (0.09 mol) of 4-[N,N-bis(hydroxyethyl)-amino]-2,2,6,6-tetramethylpiperidine,
6.28 g (0.04 mol) of 4-hydroxy-2,2,6,6-tetramethylpiperidine,
0.020 g of potassium carbonate, 6 microliters of $C_{18/6}$ crown ether.

The reaction mixture was heated at 110°–115° C. for 7 hours of 26,600 Pa.

The pressure was then progressively lowered down to 665 Pa and the temperature was maintained at 115° C. for 30 minutes.

During these operations, the methanol was removed at the rate at which it was formed, and small amounts of 4-hydroxy-2,2,6,6-tetramethylpiperidine were also removed.

The removal of the volatile compound from the reaction mixture was completed by heating at 120° C. under 266 Pa for 2 hours.

52 g of a yellow highly viscous oil were finally obtained.

IR spectrometry and NMR analyses confirmed the expected structure of the product.

EXAMPLE 5

Preparation of product (Ie):, decakis[4-(N,N-diethyleneamino-2,2,6,6-tetramethylpiperidine] undecakis(didodecyl carbonate)

A compound of the general formula (I) in which:
R = dodecyl radical
n = 10
Z = radical of formula (III)

The following were charged into a 200 cm³ roundbottomed flask fitted with a central stirrer, a thermometer pocket and a distillation column:
  49.5 g (0.138 mol) of the product (Ia) prepared in Example 1,
  27.45 g (0.113 mol) of 4-[N,N-bis(hydroxy-ethyl)amino]2,2,6,6-tetramethylpiperidine,
  9.3 g (0.05 mol) of n-dodecanol,
  0.020 g of potassium carbonate, and
  5 microliters $C_{18/6}$ crown ether.

The reaction mixture was heated at 105° C. for 4 hours under a pressure of 26,600 Pa.

The pressure was then progressively lowered down to 27 Pa and the temperature was maintained at 100°–105° C. for 2 hours, the methanol was removed at the rate at which it was formed.

81.1 g of a yellow viscous oil were finally obtained.

IR spectrometry and NMR analyses confirmed the expected structure of the product.

EXAMPLE 6

PREPARATION of product (If): pentakis[4-(N,N-diethyleneamino)-2,2,6,6-tetramethypiperidine] hexakis (didodecyl carbonate)

A compound of the general formula (I) in which:
R = dodecyl radical
n = 5
Z = radical of formula (III).

The following were charged into a 200 cm³ roundbottomed flask fitted with a central stirrer, a thermometer pocket and a distillation column,
  54 g (0.15 mol) of the product (Ia) prepared in Example 1,
  24.4 g (0.10 mol) Of 4-[N,N-bis(hydroxyethyl)-amino]-2,2,6,6-tetramethylpiperdine,
  18.6 g (0.10 mol) of n-dodecanol,
  0.020 g of potassium carbonate, and
  5 microliter of $C_{18/6}$ crown ether.

The reaction mixture was heated at 105° C. for 4 hours under a pressure of 26,600 Pa.

The pressure was then progressively lowered down to 27 Pa and the temperature was maintained at 100°–105° C. for 2 hours, the methanol was removed at the rate at which it was formed.

91.3 g of a yellow viscous oil were finally obtained.

IR spectrometry and NMR analyses confirmed the expected structure of the product.

EXAMPLE 7

Preparation of product (Ig): decamethylene bis(2,2,6,6-tetramethyl-4 piperidinyl carbonate)

A compound of the general formula (I) in which:
R = radical of formula (II) where $R_1$ = H
n = 1
Z = decamethylene radical A) Preparation of decamethylene bis(dimethyl carbonate)

The following were charged into a 1000 cm³ round bottomed flask fitted with a central stirrer, a thermometer pocket, a lateral nitrogen inlet tube and a distillation column:
  324 g (3.6 mol) of dimethyl carbonate,
  52.2 g (0.3 mol) of decane-1,10-diol, and
  0.046 g of sodium hydroxide in powder form.

The apparatus was flushed with nitrogen and the fraction mixture was then heated to 90°–92° C. under a stream of nitrogen. A methanol/dimethyl carbonate binary system was then distilled, while maintaining a high reflux rate. The temperature of the vapors, which was initially 63° C., rose progressively to 90° C. after a reaction time of 5 hours.

The temperature was then raised up to 120° C., removing virtually all of the excess dimethyl carbonate.

The remainder of the volatile products were then removed at 120° C., lowering the pressure down to 53 Pa.

84 g of a yellow viscous oil, which solidified on cooling (m.p. = about 60° C.), were finally obtained.

IR spectrometry and NMR analyses confirmed the expected structure of the product.

B) Preparation of decamethylene bis(2,2,6,6-tetramethyl-4-piperidinyl carbonate)

The following were charged into a 100 cm³ roundbottomed flask fitted with a central stirrer, a thermometer pocket, a lateral nitrogen inlet tube and a distillation column:
  29 g (0.1 mol) of the product prepared under A)
  36.1 g (0.23 mol) of 4-hydroxy-2,2,6,6-tetramethylpiperidine,
  0.032 g of potassium carbonate, and
  5 microliters of $C_{18/6}$ crown ether.

The reaction mixture was heated at 110°–115° C. for 7 hours under a nitrogen atmosphere and then for 2 hours under a pressure of 26,600Pa.

The pressure was then progressively lowered down to 665 Pa and the temperature was maintained at 115° C. for 30 minutes.

During these operations, the methanol was removed at the rate at which it was formed, and small amounts of 4-hydroxy-2,2,6,6-tetramethylpiperidine were also removed.

The removal of the volatile compounds from the reaction mixture was completed by heating at 120° C. under 266 Pa for 2 hours.

47 g of a yellow viscous oil were finally obtained.

NMR analysis confirmed the expected structure of the product.

EXAMPLE 8

Photostabilization of APPRYL 3030 P poly-propylene (PP) marketed by BP Chimie

Approximately 300 g by weight of each of the mixtures whose composition is indicated in the following table (I) were prepared in a slow mixer:

TABLE I

| Composition | A | B | C | D | E | F | G | H | J |
|---|---|---|---|---|---|---|---|---|---|
| PP | 100 | 100 | 100 | 100 | 100 | 100 | 100 | 100 | 100 |
| Ca stearate | 0.1 | 0.1 | 0.1 | 0.1 | 0.1 | 0.1 | 0.1 | 0.1 | 0.1 |
| Phenolic antioxidant* | 0.05 | 0.05 | 0.05 | 0.05 | 0.05 | 0.05 | 0.05 | 0.05 | 0.05 |
| Phosphite** | 0.05 | 0.05 | 0.05 | 0.05 | 0.05 | 0.05 | 0.05 | 0.05 | 0.05 |
| Commercial anti-UV**** CHIMASSORB944 | 0 | 0.15 | 0.30 | 0 | 0 | 0 | 0 | 0 | 0 |
| Product Ia Example 1 | 0 | 0 | 0 | 0.15 | 0.30 | 0 | 0 | 0 | 0 |
| Product Ib Example 2 | 0 | 0 | 0 | 0 | 0 | 0.15 | 0.30 | 0 | 0 |
| Product Ic Example 3 | 0 | 0 | 0 | 0 | 0 | 0 | 0 | 0.15 | 0.30 |
| Product Id Example 4 | 0 | 0 | 0 | 0 | 0 | 0 | 0 | 0 | 0 |
| Product If Example 6 | 0 | 0 | 0 | 0 | 0 | 0 | 0 | 0 | 0 |
| Product Ie Example 5 | 0 | 0 | 0 | 0 | 0 | 0 | 0 | 0 | 0 |

| Composition | K | L | M | N | P | Q |
|---|---|---|---|---|---|---|
| PP | 100 | 100 | 100 | 100 | 100 | 100 |
| Ca stearate | 0.1 | 0.1 | 0.1 | 0.1 | 0.1 | 0.1 |
| Phenolic antioxidant* | 0.05 | 0.05 | 0.05 | 0.05 | 0.05 | 0.05 |
| Phosphite** | 0.05 | 0.05 | 0.05 | 0.05 | 0.05 | 0.05 |
| Commercial anti-UV**** CHIMASSORB944 | 0 | 0 | 0 | 0 | 0 | 0 |
| Product Ia Example 1 | 0 | 0 | 0 | 0 | 0 | 0 |
| Product Ib Example 2 | 0 | 0 | 0 | 0 | 0 | 0 |
| Product Ic Example 3 | 0 | 0 | 0 | 0 | 0 | 0 |
| Product Id Example 4 | 0.15 | 0.30 | 0 | 0 | 0 | 0 |
| Product If Example 6 | 0 | 0 | 0.15 | 0.30 | 0 | 0 |
| Product Ie Example 5 | 0 | 0 | 0 | 0 | 0.15 | 0.30 |

*pentaerythrityl 3-tetra(4-hydroxy-3,5-di-tert-butylphenyl)propionate
**tris(2,4-di-tert-butylphenyl) phosphite
***CHIMASSORB 944

These compositions were extruded under the following conditions:
  THORET brand extruder:
    diameter of the screw = 20 mm
    length of the screw = 400 mm
    temperature profile:
      zone 1 = 200° C.
      zone 2 = 220° C.
      zone 3 = 220° C.
      zone 4 = 230° C.
      die head = 215° C.

The strip obtained was granulated and the granules were then pressed to give 200 μm films using a CARVER press under the following conditions:
  temperature = 210° C.
  time = 5 min.
  pressure = 20 MPa.

These films were exposed in a SAIREM-SEPAP 12-24 type accelerator aging chamber. In this chamber the samples were arranged on a cylindrical turret driven in a circular rotary movement. The turret itself was located in the center of a parallelepipedal chamber, the 4 angles of which were occupied by a MAZDA MA 400 W type "medium pressure" mercury vapor lamp.

The lamp cover permitted only the passage of radiation having a wavelength higher than 300 nm. A device of this type is described in French Patent 2,430,609.

The temperature of the chamber was maintained at 60° C. by means of a regulating system.

The aging of the films was followed by infrared spectrometry, the optical density of the carbonyl band at 1720-1740 cm$^{-1}$ reflected the degree of photooxidation of the polymer material.

The results obtained, which are collated in Table II below, indicate the time necessary to obtain an optical density of 0.3. The time necessary to obtain the optical density is the "life" of yhe composition.

TABLE II

| Composition | Anti-UV Stabilizer | Time to obtain an optical density of 0.3 |
|---|---|---|
| A | None | 40 h |
| B | CHIMASSORB 944 | 400 h |
| C | CHIMASSORB 944 | 600 h |
| D | Product Ia | 320 h |
| E | Product Ia | 400 h |
| F | Product Ib | 350 h |
| G | Product Ib | 470 h |
| H | Product Ic | 440 h |
| J | Product Ic | 600 h |

TABLE II-continued

| Composition | Anti-UV Stabilizer | Time to obtain an optical density of 0.3 |
|---|---|---|
| K | Product Id | 400 h |
| L | Product Id | 500 h |
| M | Product If | 350 h |
| N | Product If | 440 h |
| P | Product Ie | 320 h |
| Q | Product Ie | 510 h |

We claim:

1. An organic polymer composition stabilized against the harmful effects of light and ultraviolet radiation comprising an organic polymer having incorporated therein an effective amount of at least one compound containing a 2,2,6,6-tetramethyl-piperidinyl group, which compound has the general formula (I):

  (I)

in which:

R represents:

a straight-chain or branched alkyl radical having 1 to 18 carbon atoms;

a cycloalkyl radical having 5 to 12 carbon atoms;

a phenyl radical;

a phenyl radical containing 1 or 2 straight chain or branched alkyl substituents having 1 to 12 carbon atoms;

a phenylalkyl radical in which the straight-chain or branched alkyl part contains 1 to 12 carbon atoms; or a 2,2,6,6-tetramethyl-4-piperidinyl radical of formula (II)

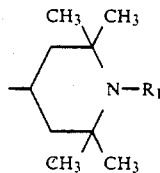

in which $R_1$ represents a hydrogen atom or a methyl radical; and

Z represents a radical of the formula (III)

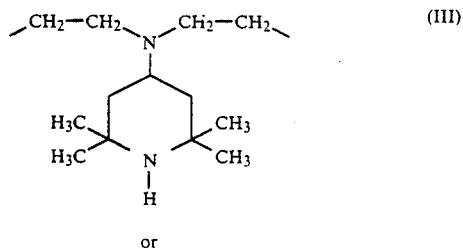

or a polymethylene group having 2 to 15 carbon atoms, provided that when Z is a polymethylene group, R is a 2,2,6,6-tetramethyl-4-piperidinyl radical of the formula (II) and n is a number from 1 to 2, and when Z is radical of formula (III), n is a number from 1 to 100.

2. The composition of claim 1, wherein the organic polymer is selected from the group consisting of polyolefins, polystyrenes, polyalcadienes, polyurethanes, polyamides, polyesters, polycarbonates, polysulfones, polyether sulfones, polyether ketones, acrylic polymers, halogenated polymers, their copolymers and mixtures thereof.

3. The composition of claim 1, wherein the organic polymer is a polyolefin or polyalcadiene selected from the group consisting of polypropylene, high density polyethylene, low density polyethylene, straight-chain low density polyethylene, polybutadiene, their copolymers or mixtures thereof.

4. The composition of claim 1, which contains from 0.004 to 20 milliequivalents, of the 2,2,6,6-tetramethyl-piperidinyl group per 100 g of polymer.

5. The composition of claim 1, which contains from 0.020 to 4 milliequivalents of the 2,2,6,6-tetramethyl-piperidinyl group per 100 g of polymer.

* * * * *